United States Patent [19]

Wright

[11] Patent Number: 4,986,276
[45] Date of Patent: Jan. 22, 1991

[54] FLOW DETECTOR

[76] Inventor: Terry Wright, 11023 118th Pl. NE., Kirkland, Wash. 98034

[21] Appl. No.: 355,692

[22] Filed: May 22, 1989

[51] Int. Cl.⁵ .............................................. A61B 8/00
[52] U.S. Cl. ........................... 128/662.04; 128/662.01
[58] Field of Search ...................... 128/661.06, 662.03; 73/861.25

[56] References Cited

U.S. PATENT DOCUMENTS 4,796,634  1/1989  Huntsman et al. ............. 128/662.01

OTHER PUBLICATIONS

Wells, P. N. T. "Biomedical Ultrasonics", Academic Press, N.Y. 1977 pp. 63–64.

Primary Examiner—Francis Jaworski
Attorney, Agent, or Firm—John E. Wagner

[57] ABSTRACT

An ultrasonic, transcutaneous blood flow detector. A protective mounting cup is positionable against the skin of a patient for the transfer of ultrasonic energy into and out of the patient's body. The detector utilizes only a single piezoelectric transducer with a first face in juxtaposition with an interior face of the cup. A film of viscous semifluid material is positioned between the transducer first face and the cup's interior face to couple ultrasonic energy between the transducer and the cup. A resilient spring or foam member resiliently biases the transducer first face into engagement with the cup's interior face with the semifluid material therebetween, thus permitting substantially uninhibited deformation of the transducer in response to a drive signal. A transmitter supplies a continuous wave drive signal to the transducer, and a detector circuit operating concurrently therewith detects the Doppler frequency shifted electrical signal generated by the transducer as a result of the Doppler frequency shifted acoustic energy reflected back to the transducer. The transmitter provides the drive signal to the transducer with an output voltage automatically variable in response to loading of the transducer with reflective energy. An amplifier and audio binaurals provide a variable pitch audible tone to the user.

36 Claims, 3 Drawing Sheets

FIG. 8

FLOW DETECTOR

This application is a substitute for application Ser. No. 039631 filed Apr. 17, 1987.

TECHNICAL FIELD

The present invention relates generally to flow detectors, and more particularly, to an ultrasonic, transcutaneous blood flow detector for detecting the blood flow in a patient's body. The invention is also usable for detecting fluid flows in other bodies.

BACKGROUND ART

Ultrasound diagnostic equipment has long been used in the medical field to detect the flow of blood. Conventionally, the velocity of the blood is sensed by taking advantage of the Doppler frequency shift that occurs when the ultrasonic energy engages the moving blood. Conventional ultrasonic flow detectors generally utilize one of two transducer arrangements. One arrangement utilizes a single transducer operating in a pulsed mode. A transmitter is used to excite the transducer to transmit a brief pulse of ultrasonic energy, and then the transmitter is turned off. During the off-time and for the period prior to the next transmit pulse, the detector circuitry senses any signal produced on the transducer from the return reflected energy.

An alternative arrangement utilizes dual-transducers operating in a continuous wave mode. The transmitter operates by continuously sending ultrasonic energy from one of the transducers, while the return reflected energy is being simultaneously sensed by the second transducer. The two transducers effectively operate independent of each other. The continuous wave approach with dual-transducers requires a more complex transducer design and inherently has sensitivity limitations relating to the distance between the transducers and the area of reflection within the patient's body. Generally, the transducer elements are side-by-side pointing along parallel beam paths, so the transmit energy beam does not line up perfectly with the reflected energy beam. As such, reception is limited to the incidental scattering of the transmit beam. In the past, attempts have been made to overcome this limitation by lensing the acoustic beams to produce a beam crossover point at some distance from the transducers. While this produces a good result as long as the area of reflection within the body is at the depth of penetration at which the beams are focused, reception outside of this limited area is not good.

While the single transducer operating in a pulsed mode as first discussed is generally a more expensive design to manufacture, it does overcome some of the problems associated with using dual-transducers with focused beams. This is because the transmitted energy and the received reflected energy travel along the same straight line path. Even with a single transducer operating in the pulse mode, the transducer will not work equally well at all distances from the transducer because the pulse rate used limits the reception window available due to the fixed speed of the acoustic wave traveling through the body.

In conventional blood flow detector designs, the transducer units are manufactured with one of three techniques. The first technique has the transducer clamped in position to a protective face plate using mounting screws or rings. In addition to protecting the transducer, the face plate can be provided with a thickness equal to a desired odd number of quarter-wave lengths of the acoustic output signal of the transducer for impedance matching and tuning. Alternatively, a second technique bonds the transducer to the face plate with an adhesive compound. The third technique has the protective face plate for the transducer being formed from the adhesive itself applied directly to the transducer. In each of these designs, the active transducer may or ay not be backed with an absorptive or reflective substance. In any event, the active element is rigidly attached to the face late and any flexure of the transducer or face plate may damage the transducer which is usually made of a brittle ceramic. Furthermore, mechanical impact, thermal variations and aging of the bonding agents used may cause the transducer to detach. Thermal variations or mechanical stress can cause the Q factor of the transducer to vary, and hence change its resonant frequency. In addition to these problems since the transducer is mechanically strained and restrained, either by the clamping or the adhesive used, the process of mounting the transducer to the protective face plate affects the operation of the transducer.

Another disadvantage experienced with the assembly of conventional transducer units using adhesive is a high rate of rejection due to the formation of micro-bubbles in the bond layer. The bubbles have an adverse impact on the ultrasonic energy passing through the bond layer.

It will therefor be appreciated that there is a significant need for an ultrasonic fluid flow detector which avoids these disadvantages. The flow detector should be inexpensive to manufacture and have a high manufacturing yield rate. The detector should be very sensitive, have a good signal-to-noise ratio, and have good spacial resolution and definition. The present invention avoids these disadvantages and fulfills these needs, and further provides other related advantages.

DISCLOSURE OF THE INVENTION

The present invention resides in an ultransonic flow detector for detecting the flow of fluid in a body. The disclosed embodiment is a transcutaneous blood flow detector. The detector includes a single piezoelectric transducer for the transfer of ultrasonic energy into and out of the body. The transducer is deformable in response to an electrical drive signal applied thereto and received ultrasonic acoustic energy reflected from within the body.

The detector has transmitter means connected to the transducer for supplying the drive signal to the transducer. The drive signal is a continuous wave excitation signal causing the transducer to continuously transmit an acoustic output signal at a desired transmitted ultransonic frequency. A detector means is connected to the transducer and operates concurrently with the transmitter means for detecting a Doppler frequency shifted electrical signal generated by the transducer as a result of Doppler frequency shifted acoustic energy reflected back to the transducer from within the body indicative of fluid flow. The detector means generates a detected signal in response thereto, indicative of velocity changes in the detected fluid flow.

Output means are connected to the detector means for providing an output signal to the user responsive to the detector signal to indicate to the user the detected fluid flow. As such, the flow detector operates with a single transducer continuously transmitting the acoustic output signal while concurrently detecting any Doppler frequency shifted acoustic energy reflected back to the transducer using the same transducer without use of pulsing. The transmitted acoustic output signal and the Doppler frequency shifted acoustic reflected energy travel along the same straight line path between the transducer and the area of reflection within the body to avoid focusing problems.

In the presently preferred embodiment of the invention, the detector includes a transducer mounting member having an exterior face positionable against the body for the transfer of ultrasonic energy into and out of the body, and an opposite interior face. The interior face is mounted in juxtaposition with a first face of the transducer, and the transducer has an opposite second face. The transducer is substantially freely movable laterally and axially relative to the mounting member within at least a range sufficient to permit substantially uninhibited deformation of the transducer in response to the drive signal applied thereto and received ultrasonic acoustic energy reflected from within the body. A film of viscous semifluid material is positioned between the transducer first face and the mounting member interior face to couple ultrasonic energy between the transducer and the mounting member. A resilient member resiliently biases the transducer first face into engagement with the mounting member interior face with the film of viscous semifluid material therebetween.

In a preferred embodiment of the invention, the mounting member includes an annular sidewall extending about the perimeter of the transducer spaced away from a perimeter edge wall of the transducer to provide a free edge space therebetween, and defines an interior chamber. A pedestal is positioned generally centrally within the chamber extending away from the exterior face and terminating in the interior face. The pedestal and sidewall define an interior annular wall extending between the pedestal and the sidewall, and spaced away from the interior face toward the exterior face. The pedestal interior face is sized smaller than the transducer first face to provide the transducer first face with an annular edge portion extending laterally beyond the interior face. The annular edge portion is held spaced away from the inward annular wall. With this design, the Q factor of the transducer is increased.

To further increase the Q factor of the transducer, the interior and exterior faces of the mounting member are separated by an even number of quarter-wave lengths of the acoustic output signal. With this arrangement, unlike with the conventional odd number of quarter-wave lengths used to match impedances, the ultransonic energy of the acoustic output signal transmitted by the transducer which fails to cross the boundary between the exterior face and the body against which the exterior face is positioned is intentionally reflected back to the transducer in phase, thus increasing the transducer impedance and the Q factor.

The transmitter means includes drive means for providing the drive signal to the transducer with an output voltage variable in response to loading of the transducer with reflective energy, with the frequency of the drive signal being automatically variable in response to variations in the loading of the transducer. This achieves optimal operational frequency of the transducer within a range of optimal operational frequencies.

In the presently preferred embodiment, the drive means includes an oscillator providing an output signal, and an impedance transformer connected to the oscillator. The transformer transforms the oscillator output signal to a high voltage, low current signal comprising the transducer drive signal, and the output signal has an output voltage variable in response to the loading of the transducer. The impedance transformer includes an inductor connected in series between the oscillator and the transducer, and a capacitor connecting in parallel with the transducer and operating with the inductor to form a high impedance drive circuit to the transducer. As such, the noise generated by the oscillator is supplied to the transducer at high impedance, and if outside the resonant frequency domain of the transducer are effectively filtered out by the transducers mechanical nonresponsiveness thereto. Preferably, the oscillator output signal is at a substantially constant current.

Other features and advantages of the invention will become apparent from the following detailed description, taken in conjunction with the accompanying drawings.

BEST MODE FOR CARRYING OUT THE INVENTION

Figure 1:
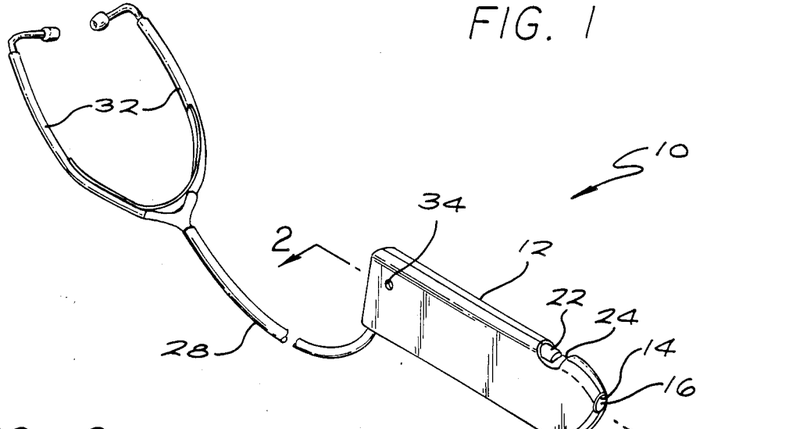
FIG. 1 is a fragmentary isometric view of an ultransonic, transcutaneous blood flow detector embodying the present invention.
Figure 2:
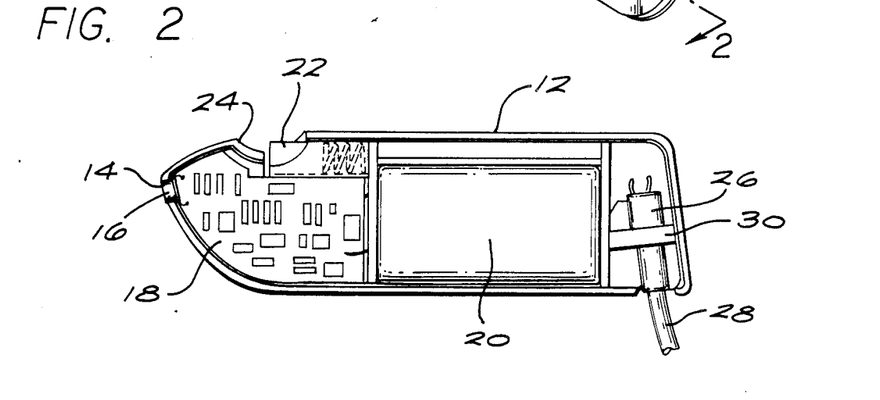
FIG. 2 is a fragmentary, enlarged sectional view taken substantially along the lines 2—2 of FIG. 1.

As shown in the drawings for purposes of illustration, the present invention is embodied in an ultransonic, transcutaneous blood flow detector, indicated generally by reference number 10, for detecting the flow of blood in a patient's body (not shown). The blood flow detector 10 includes a housing 12 having an aperture 14 at a forward end thereof in which is positioned a transducer assembly 16, as shown in FIGS. 1 and 2. The housing also contains therein a printed circuit board 18 on which the circuitry for the blood flow detector 10 is mounted. A battery 20 is positioned within the housing 12 to provide power for the circuitry on the printed circuit board 18. A spring mounted slide switch button 22 protrudes into an indentation 24 in the housing 12 and is positioned for actuation by the finger of the user. The switch activated by the button 22 turns power from the battery 20 on and off to the circuitry on the printed circuit board 18. The housing 12 in the presently preferred embodiment of the invention is approximately 10.8 cm in length, 3.18 cm in width and 1.5 cm in depth, with a weight of 59 gm, to provide a compact and easy to carry and handle design.

When blood flow is detected, the transducer assembly 6 and the circuitry on the printed circuit board 18, operating as will be described in more detail below, generate an output signal which is supplied to an audio speaker 26 mounted within the housing 12 (see FIG. 2). The speaker 26 generates a variable pitch audible tone with variations in pitch which indicate velocity changes of the detected blood flow. The audible tone is transmitted through a hollow acoustic tube 28 to a set of stethoscope binaurals 32 positionable at the user's ears for transmitting the audible tone to the user's ears. One open end of the tube 28 terminates at a bracket 30 positioned within the housing 12 and in front of the speaker 26 for transmission of the audible tone into the tube. The other open end of the tube 28, in conventional fashion, is connected to the binaurals 32 which comprise a pair of hollow acoustic tubes acoustically coupled together and to the tube 28.

The housing 12 is further provided with an aperture 34 (see FIG. 1) for access to a variable resistance pot 36 (see FIG. 7) positioned within the housing 12 for making any volume adjustment settings necessary to provide a comfortable volume level for the user. Once set, the volume will likely not have to ever be readjusted.

Figures 3, 4:
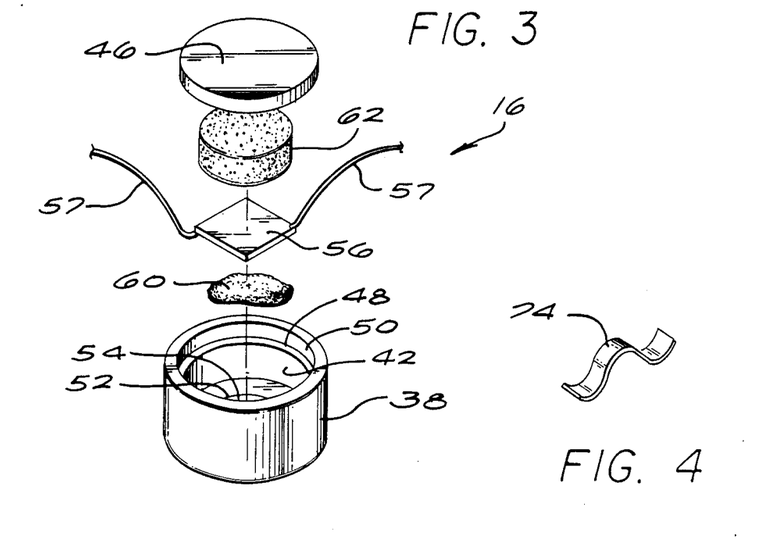
FIG. 3 is an enlarged, exploded isometric view of the transducer assembly with a resilient foam member holding a transducer in place as used in the blood flow detector of FIG. 1, shown disassembled from the remainder of the detector.
FIG. 4 is an isometric view of a wave spring usable in an alternative embodiment of the invention in place of the resilient foam shown in FIG. 3.
Figures 5, 6, 7:
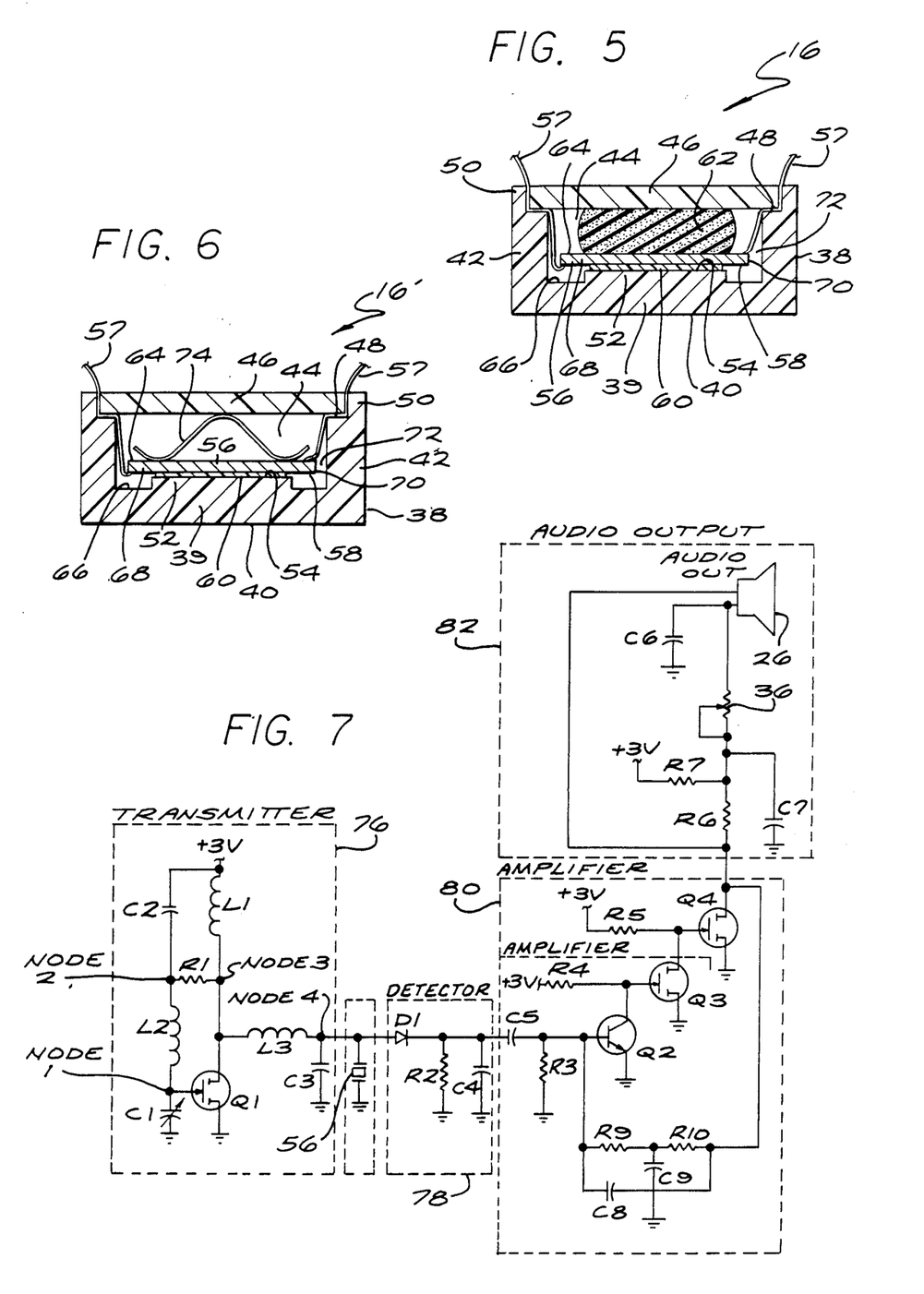
FIG. 5 is an enlarged, sectional side elevational view of the embodiment of the transducer assembly of FIG. 3.
FIG. 6 is an enlarged, sectional side elevational view of an alternative embodiment of the transducer assembly of FIG. 3 utilizing the wave spring of FIG. 4 to hold the transducer in place.
FIG. 7 is a schematic diagram showing the electronic circuitry used with the blood flow detector of FIG. 1.

As best shown in FIGS. 3 and 5 for a first embodiment of the invention, the transducer assembly 16 includes a mounting cup 38 with a front wall 39 having an exterior face 40 positionable against the skin of the patient for the transfer of ultransonic energy into and out of the patient's body. The mounting cup 38 has a cylindrical annular sidewall 42 defining an interior chamber 44. The chamber 44 is closed at one end by the front wall 39 and at an opposite end by a cap disc 46. The disc 46 is received against an interior stop shoulder 48 formed in an end portion 50 of the annular sidewall 42 spaced away from the front wall 39. The front wall 39 has formed integral therewith a cylindrical pedestal 52 positioned generally centrally within the interior chamber 44 and extending away from the exterior face 40 and terminating in a circular interior face 54 within the chamber.

A single piezoelectric transducer 56 is positioned within the chamber 44 of the mounting cup 38, and has a circular first face 58 mounted in face-to-face juxtaposition with the pedestal interior face 54. A pair of wire leads 57 extend from the transducer 56 and between the cap disc 46 and the annular sidewall 42 to the exterior of the mounting cup 38. The transducer 56 is freely movable laterally and axially relative to the mounting cup 38 within at least a range sufficient to permit substantially uninhibited deformation of the transducer in response to an electrical drive signal applied thereto and received ultrasonic acoustic energy reflected from within the patient's body. A film of viscous semifluid material 60, shown with an exaggerated thickness for purposes of illustration in FIG. 5, is positioned between the transducer first face 58 and the pedestal interior face 54 to couple ultrasonic energy between the transducer 56 and the mounting cup 38. The semifluid material 60 provides a fluidized plastic interface which prevents an air boundary from forming between the transducer 56 and the pedestal 52.

A resilient foam disc 62 is positioned within the interior chamber 44 between the cap disc 46 and a second side 64 of the transducer 56 which is parallel with an opposite the transducer first face 58. The foam disc 62 is held in a compressed state in yieldable engagement with the disc cap and the transducer second face. The foam disc 62 resiliently biases the transducer first face 58 into engagement with the pedestal interior face 54 with the film of viscous semifluid material 60 therebetween.

The annular sidewall 42 and the pedestal 52 defined therebetween an inward annular wall 66, inward of the exterior face 40 and spaced away from the pedestal interior face 54 toward the exterior face. The transducer 46 is of a diameter larger than the diameter of the pedestal 52 and is centrally positioned on the pedestal in coaxial alignment therewith. As such, an annular edge portion 68 of the transducer extends laterally outward beyond the perimeter of the pedestal interior face 54. The annular edge portion 68 of the transducer 56 is held spaced away from the inward annular wall 66. The annular sidewall 42 has a diameter sized to position it laterally spaced apart from a perimeter edge wall 70 of the transducer 56 to provide a free edge space 72 therebetween. For purposes which will be described in more detail below, this arrangement provides a transducer assembly 16 with the transducer 56 mounted in a manner which promotes superior transducer performance.

Prior art transducer assemblies in which the transducer is clamped in position to a protective face plate using mounting screws or rings, or is bonded to the face plate using an adhesive compound or embedded in an adhesive to form the face plate, mechanically strain the transducer and restrain its free movement in response to electrical signals and received ultrasonic acoustic energy reflective from within the patient's body. In the present invention, the transducer 56 is mounted in a "floating" or loosely held state, and is not bonded or otherwise restrained except for the slight biasing force applied thereto by the resilient foam disc 62 to hold the transducer in place on the pedestal 52. As such, sonic coupling of the transducer 56 to the protective front wall 39 is achieved while eliminating any mechanical coupling. It has been found that unlike with prior art transducer assemblies, the mounting technique of the present invention has little impact upon the operating characteristics and responsiveness of the transducer 56 and provides a higher Q factor for the transducer. Furthermore, flexure of the front wall 39 or the transducer 56 itself, mechanical impact and thermal variations cause little change in the operating characteristics of the transducer and will not damage the transducer.

With the invention, the natural action of the transducer 56 to shrink and expand both axially and laterally in response to the electrical drive signal applied thereto or receive ultrasonic acoustic energy reflected from within the patient's body is not inhibited as by the clamping and bonding used in prior art transducer assemblies. The result is a transducer having a Q factor and a resonant frequency which do not change as drastically as with prior art transducer assemblies from the mechanical and thermal stresses applied thereto during use. In addition, the mounting of the transducer 56 on the pedestal 52 with the annular edge portion 68 extending beyond and held free from engagement with the pedestal interior face 54, and with the perimeter edge wall 70 of the transducer positioned away from the annular sidewall 42 limits the interface area with the mounting cup 38 and thereby increases the mechanical Q factor of the transducer. The increased Q of the transducer 56 causes the transducer to effectively function as a mechanical filter, reducing the transmitter noise passed to the detector used.

In addition to eliminating most of the common failure modes encountered with prior art transducer assemblies, the mounting technique of the present invention increases the ease of production and reduces defective mountings, and thus increases the manufacturing yield rate. As noted above, the operating characteristics of the transducer 56 are also favorably changed. Another benefit is in the reduced cost to manufacture since only a single transducer is used without going to a pulsed mode operation.

The semifluid material 60 may be a high viscosity oil or plastic having good wetting properties and sufficient adherence so that it will stay on and between the pedestal interior face 54 and the transducer first face 58 even if the blood flow detector 10 is turned on its side for prolonged periods of time. The semifluid material should exhibit little, if any, oxidation or decay over prolonged periods. As previously noted, the semifluid material is provided to eliminate the possibility of an air gap forming between the transducer 56 and the pedestal 52 which would degrade performance of the transducer and hence the blood flow detector. The thickness of the film of semifluid material 60 is expected to be approximately 0.1 thousandths of an inch thick. It is presently preferred to use as the semifluid material 60 an amine grated ethelyne/propolene copolymer including chemically neutralized napthenic petroleum distillates, solvent de-waxed heavy parafinic petroleum distillates, zinc dialkyldithiophosphate and calcium sulfonate.

An alternative embodiment of the transducer assembly 16' is shown in FIG. 6. In this embodiment, the resilient foam disc 62 is replaced with a thin strip wave spring 74, such as shown in FIG. 4. The spring 74 is selected so as to be substantially inactive at the ultransonic frequency at which the transducer is operated. The spring 74 may also be configured as a leaf or coil spring, and can be manufactured of metal, plastic, fiberglass or graphite fibers.

Turning now to FIG. 7, the electrical drive signal is applied to the transducer 56 by a transmitter 76, shown schematically in FIG. 7 and comprising a portion of the circuitry on the printed circuit board 18. The drive signal is a continuous wave excitation signal which causes the transducer 56 to continuously transmit an acoustic output signal at a desired transmitted ultrasonic frequency. In a presently preferred embodiment of the invention, a transducer is operated at 4.9 MegaHertz. At this frequency in transcutaneous mode, the blood flow detector 10 can detect venous and arterial blood flow in peripheral vessels since any movement occurring within the range of the acoustic signal creates a Doppler shift in the vibrations reflected back to the transducer.

In the past, electro-strictive transducers, such as the type used for the transducer 56 in the presently preferred embodiment of the invention, utilized transmitter circuitry consisting of an oscillator and a driver stage. The transmitter circuitry comprised a voltage source providing drive to the transducer, usually with an inductor in parallel therewith to resonate with the capacitance of the transducer. When driven in this mode, the voltage on the transducer is constant, regardless of the load or reflected energy, at least within the current limits of the driver stage. As such, any signal on the transmitting transducer as a result of received ultransonic acoustic energy reflected back from within the patient's body was virtually undetectable and hidden in noise. In the present invention, the circuitry of transmitter 76 includes an oscillator portion and a driver portion, as will be described in more detail below, however, unlike with the prior art, the circuitry is designed so that the transmitter 76 behaves as a constant current source, rather than a constant voltage source, and the transducer 56 acts as if it were driven by a high impedance source. The voltage on the transducer 56 fluctuates as the load on the transducer changes. This is accomplished in part by driving the transducer 56 from the center point of an LC network with the center point being a high impedance node at the junction of an inductor L3 and a capacitor C3.

Since the single transducer 56 is used both to transmit the acoustic output signal at the desired transmitted ultransonic frequency and to receive the ultrasonic acoustic energy reflected from within the patient's body, it is important that significant voltage fluctuations be realized across the transducer in response to the received reflected energy. This is necessary so that the received reflected energy can be sensed by a detector 78, shown schematically in FIG. 7. As noted above, this is to be compared with a conventional transducer drive circuitry which caused the voltage on the transducer to remain constant regardless of the load or received reflected energy. With the present invention, heterodyning of the out of phase signals reflected from within the patient's body due to the Doppler frequency shift reduce the voltage across the transducer 56, and in phase signals increase the voltage. These voltages are detected by the detector 78 using a simple, direct half-wave rectifier arrangement with a diode D1 rather than a complicated detector circuit. The heterodyning takes place within the crystal of the transducer 56 itself, and the detected voltage variations on the transducer contain the audio information used to generate the variable pitch audio tones indicative of velocity changes of the detected blood flow.

With past designs, there have been two inherent problems in allowing the frequency of oscillation to be controlled by the electro-strictive transducer. One problem results because most oscillator designs employ M field feed back to control regeneration. Consequently, the oscillators tend to move toward a frequency which generates the highest circulating currents in the output tank circuit, as this condition results in the greatest feed back voltage in the input tank circuit. When the transducer is connected directly to an M field oscillator, the frequency will mode hop to about 60% of the mechanical resonance, as this usually is the lowest impedance point of the electrical and mechanical transfer function of the transducer.

A second problem results because the impedance of the electro-strictive transducer is capacitive below resonance and inductive above resonance. This is the reverse of the impedance change which would provide correction in the proper direction. In other words, if the frequency falls below nominal, the transducer introduces a capacitive reactance, which will cause the frequency of an M field oscillator to fall still lower. This assumes that the transducer is loaded. Because of these problems it has been standard practice to use an oscillator to feed a buffer, which isolates the oscillator from the transducer. Such is not necessary with the transmitter 76 of the present invention.

As shown in FIG. 7, the transmitter 76 includes an inductor L1 connected between a 3 volt DC voltage supply and the drain of a field effect transistor Q1. The source of the transistor Q1 is connected to round. A capacitor C2 is connected by one terminal to the voltage supply and by an opposite terminal to one terminal of an inductor L2. The other terminal of the inductor L2 is connected to the gate of the transistor Q1. The gate of the transistor Q1 is also connected to ground through a variable capacitor C1. To assist in the further description of the circuitry, the node between inductor L2, capacitor C1 and the gate of the transistor Q1 will be referred to as "Node 1"; the node between the capacitor CS and the inductor L2 will be referred to as "Node 2"; and the node between the inductor L1 and the drain of the transistor Q1 will be referred to as "Node 3".

The circuitry of the transmitter 76 further includes a resistor R1 connected between Node 2 and Node 3, and the previously referred to inductor L3 has one terminal connected to Node 3 and an opposite terminal connected to one terminal of the transducer 56. The node between the inductor L3 and the terminal of the transducer 56 will be referred to as "Node 4". The previously referred to capacitor C3 has one terminal connected to Node 4, and an opposite terminal connected to ground, to place the capacitor in parallel with the transducer 56. It is noted that the anode of the previously referred to diode D1 of the detector 78 is also connected to Node 4.

Figure 8:
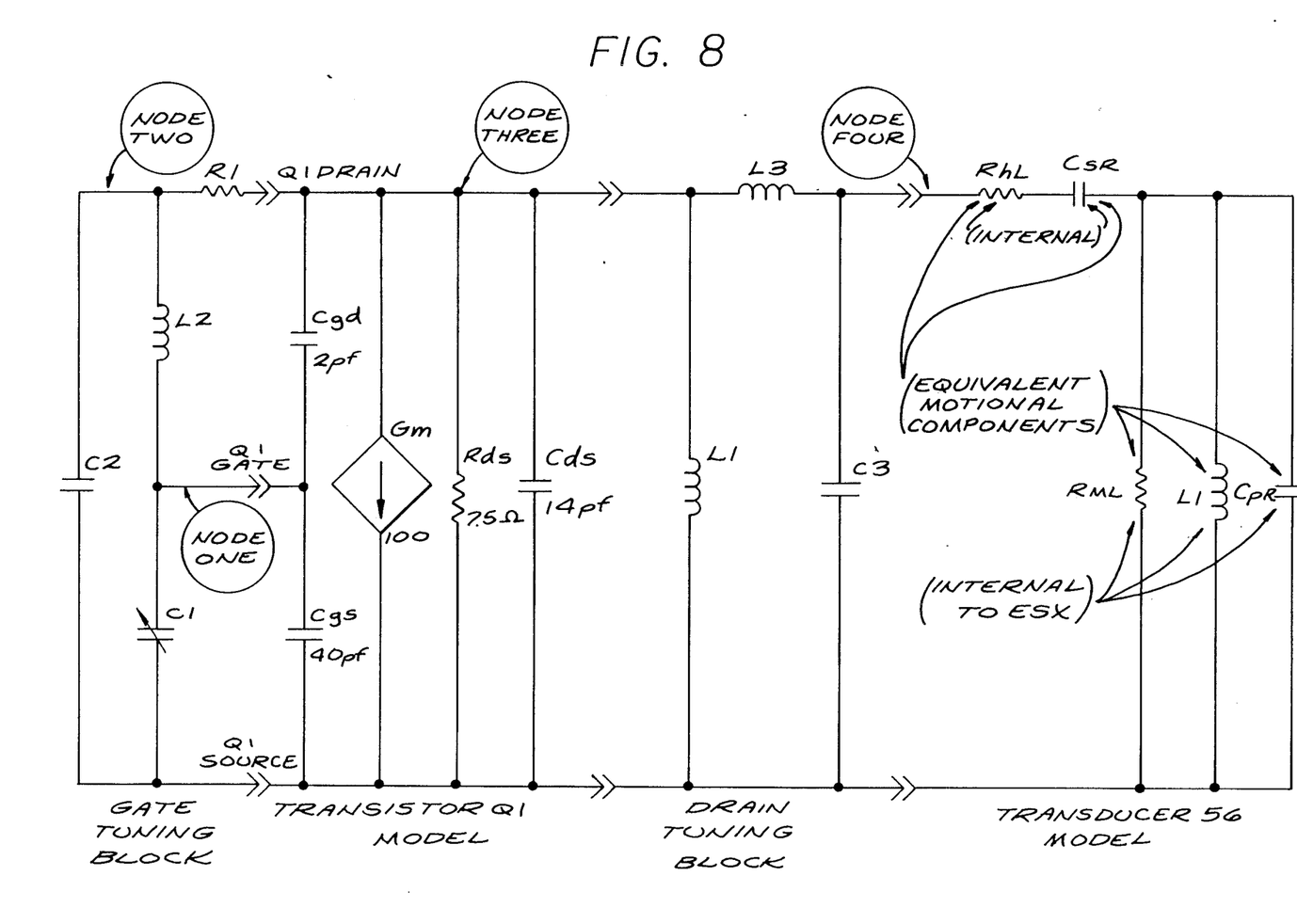
FIG. 8 is an AC equivalent circuit diagram for the transmitter circuit and transducer shown in FIG. 7.

To assist in the description of the operation of the circuitry, the oscillator used in the transmitter 76 of the present invention, which is shown schematically in FIG. 7, is drawn in an AC equivalent circuit form in FIG. 8. This equivalent circuit will now be described with reference to FIG. 8.

Gain Block

The transistor Q1 is modeled as a voltage controlled conductance with current and voltage gain. The input to transistor Q1, at Node 1, draws virtually no direct current but has reactive admittance in the form of capacitances from gate to drain Cgd and gate to source Cgs. The capacitance Cgd is small enough to be ignored.

Gate Tank

The gate of transistor Q1 is tuned by the inductor L2, the capacitor C2, and the capacitor C1 in parallel with the capacitance Cgs of the transistor Q1. The voltage at Node 1 is nearly 180 degrees out of phase with the voltage at Node 2. The capacitor C1 and the capacitance Cgs are selected for an impedance of approximately half of the impedance of the inductor L2. The combination of these three elements form a series LC network and cause the 180° phase rotation between Node 1 and Node 2. The net impedance of this series network is inductive, typically in the vicinity of j450. The capacitor C2 is selected for an equivalent −j operator. Consequently, the sum of the reactive elements in the gate tuning circuit is near enough to a condition of parallel resonance to present a relatively high impedance at Node 2. Because of this high impedance, the resistor R1 can be inserted without a great deal of loss. The resistor R1 serves to decouple Node 2 from Node 3, and limits the degree of control which the transducer 56 exercises over the oscillator frequency.

Drain Tank

The drain of the transistor Q1 is tuned by the capacitance Cds of the transistor Q1, in parallel with the inductor L1 and the series combination of the inductor L3 and the capacitor C3, with the capacitor C3 being in parallel with the transducer 56.

When the transducer 56 is not mechanically loaded and the oscillator is tuned below mechanical resonance, the transducer and the capacitor C3 present an inductive load to the inductor L3. The net j operator presented to Node 3 by the inductor L3, the capacitor C3 and the transducer is position. It is noted that under these conditions, an increase in the capacitance present at Node 4 increases the frequency of oscillation.

If a mechanical load is placed on the transducer 56 when the frequency is below mechanical resonance, it has the effect of causing partial mechanical clamping of the transducer. The clamped transducer no longer displays the net inductive behavior which occurs due to inertia in the free transducer material, and the capacitive behavior of the transducer 56 becomes dominant. Since this increase in capacitance is applied to Node 4, it increases the frequency of oscillation, as noted in the foregoing paragraph.

At mechanical resonance, the impedance of the transducer 56 is resistive, and loading produces no reactive changes and causes no change in the frequency of oscillation.

When the oscillator is tuned above mechanical resonance, the transducer 56 presents a capacitive load to the inductor L3 if it is not loaded. When the transducer 56 is loaded, the net capacitive impedance is reduced due to the resultant increase in inductive behavior and the frequency of oscillation will decrease toward optimum frequency.

In addition to providing the necessary reactances to cause mechanical loading to tune the oscillator frequency properly, the gate tank components, inductor L3 and capacitor C3, function as an impedance transformer. This definition is substantiated by the relative voltages at Nodes 3 and 4. For example, when 5 volts RMS exist at Node 3, the resultant voltage at Node 4 will be 10–15 volts RMS, depending on load. The net impedance at the inductor-capacitor L3-C3 node (Node 4) is therefore greater than the impedance at the inductor-inductor L3-L1 node (Node 3), which is the basis for the functional description of these components as an impedance transformer.

The following is a series of frequency measurements actually taken from a transmitter 76 constructed according to the invention and measured as follows: First the oscillator was adjusted to the frequency listed under the "No load" column heading, while the transducer was not loaded. Then the tip of a finger was applied to the transducer and the frequency listed under the "Loaded" column heading was recorded, with no intervening adjustment of the oscillator tuning capacitor. The numbers listed under the "Pull" column heading are the "Load frequency minus the "No load" frequency, and represent the oscillator's ability to the optimum frequency of the transducer 56. The frequency was determined to be approximately 4.988 Mhz, using a plot generated by computer comparing the loaded vs unloaded impedances of the transducer.

| Frequency (Mhz) | | |
| --- | --- | --- |
| No load | Loaded | Pull (Khz) |
| 4.820 | 4.849 | +29 |
| 4.830 | 4.866 | +33 |
| 4.840 | 4.884 | +44 |

-continued

| No load | Frequency (Mhz) Loaded | Pull (Khz) |
|---|---|---|
| 4.850 | 4.900 | +50 |
| 4.860 | 4.916 | +56 |
| 4.870 | 4.931 | +61 |
| 4.880 | 4.948 | +68 |
| 4.900 | 4.976 | +76 |
| 4.910 | 4.986 | +76 |
| | will not free run | |
| 5.000 | 4.989 | −11 |
| 5.010 | 4.996 | −14 |
| 5.020 | 4.999 | −21 |
| 5.030 | 5.009 | −21 |
| 5.040 | 5.018 | −22 |
| 5.050 | 5.026 | −24 |
| 5.060 | 5.032 | −28 |
| 5.070 | 5.040 | −30 |
| 5.080 | 5.037 | −33 |
| 5.090 | 5.056 | −34 |
| 5.100 | 5.064 | −36 |

The transducer model is extremely complicated because the mechanical constraints of acceleration, displacement and inertia correlate to inductive or capacitive elements in a convoluted fashion involving the frequency of oscillation, the degree of mechanical coupling or clamping, and internal losses or mechanical transforms which are dependent on the coupling coefficient of the material used.

It is important to discriminate between the behavior of a transducer when it is loaded as opposed to when it is unloaded.

The net impedance presented by a loaded transducer is capacitive when oscillation is below mechanical resonance, and is inductive if the oscillation frequency is above mechanical resonance. The net impedance presented by an unloaded transducer is inductive, or at least less capacitive when oscillation is below mechanical resonance, and is capacitive, or at least less inductive when oscillation frequency is above mechanical resonance.

The selected values for the inductor L1, the inductor L3 and the capacitor C3 are such that an increase in the mechanical load on the transducer 56 is reflected to the transistor Q1 as a variation in oscillator load or reactance. The result of this load reflection is an oscillator which tunes itself to the optimum operation frequency of the transducer. This self-tuning feature is very desirable in that it compensates for variations in coupling, thermal variations in the transducer, and aging of the electrical components. Should drift of the frequency result from thermal variations or coupling, for example, the oscillator frequency will pull in the proper direction to achieve an optimum operational frequency for the transducer within a range of optimum operational frequencies.

With the design of the transmitter 76 of the present invention, less precise tuning is required than in prior art devices where two stages were normally used to stabilize the frequency of operation because the transducer pulled the oscillator in the wrong direction if drift occurred. The oscillator configuration of the present invention is stable and self-adjusting, and requires fewer components than the transmitters of the prior art. Thus, a simplified and less expensive circuit design is achieved.

In the past, it was generally necessary to dampen the transducer to broaden its frequency band of operation to accommodate frequency drift in the oscillator frequency and variations in the inherent resonant frequency of the transducer. This resulted in decreasing the sensitivity of the transducer. Dampening was accomplished by adding a reflective or absorptive material backing for the transducer. While dampening of the transducer broadened the frequency band, it also made the circuit more sensitive to noise. With the design of the present invention, no dampening of the transducer 56 is necessary and a high Q factor can be maintained for the transducer. The oscillator of the transmitter 76 self tunes to stay within the desired band of operation and thus allows use of a high Q transducer. One advantage realized is that the transducer 56 with its high Q (and narrow frequency band width) is much less sensitive to noise and effectively filters out much of the nose encountered. Noise is, of course, normally intrinsic with a transistor based transmitter.

As shown in the AC equivalent circuit of FIG. 8, a simple model of the transducer 56 consists of 2 capacitors, 2 resistors and 1 inductor (the components to the right of Node 4). the values of these components change as a result of frequency and/or mechanical stress. The resistances are particularly responsive to mechanical stress, which should be understood to include both static stresses such as clamping or deformation, and dynamic stresses such as bi-modal oscillation or dynamic loading by the action of mechanical stresses which are out of phase with the primary transducer deformation.

If mechanical stresses are reflected to the transducer 56 from a media boundary which is located an odd number of quarter-waves from the transducer, they will be out of phase with the stresses originating within the transducer as a result of the applied voltages. A 90° phase shift occurs between the transducer and the reflective boundary, and a further 90° shift occurs on return, so that the stress arrives at 180° out of phase. Effectively, this out of phase stress restricts the deformation response of the transducer 56 to the applied voltage of the drive signal. In the transducer model, this situation is depicted as a reduction in the value of the resistance in the parallel L-C-R leg of the circuit. Consequently, the Q factor of the transducer falls, the transducer must be driven harder to achieve the same mechanical results, and the ability of the transducer to filter out noise decreases. The conventional approach used with transducers has, in the past, been to produce a "matched" transducer by selecting a material for use as the protective face plate with a mechanical impedance having a value between the expected impedance of the patient's body and the impedance of the ceramic material of the transducer. After the matching material was selected, the sound velocity in the material was calculated and the material was formed into a thickness which caused the selected ultrasonic frequency to transverse the material in odd numbers of quarter-wave lengths. This odd quarter-wave matching is conventional in the industry for producing a wide band of usable frequency responses, and optimum coupling.

With the present invention, the front wall 39 of the mounting cup 38 serves as the face plate, and the distance between the exterior face 40 of the front wall and the interior face 54 of the pedestal 52 is selected in an even number of quarter-wave lengths, rather than the conventional odd number of quarter-wave lengths. This even number of quarter-wave lengths represents the distance between the first face 58 of the transducer 56 and the exterior face 40 of the front wall 39 which is positionable against the skin of the patient. With this arrangement, any ultransonic energy which fails to transverse the boundary between the front wall 39 and the skin of the patient and is reflected back to the transducer 56 and returned in phase with the mechanical stresses in the transducer. This is to be compared with conventional odd quarter-wave matching where the return of such reflected ultrasonic energy would be out of phase. Since the reflected ultrasonic energy is in phase, the Q factor of the transducer 56 is increased, thus improving its noise filtration capabilities and increasing the responsiveness of the transducer to received ultrasonic acoustic energy reflected back to the transducer from within the patient's body. As previously described, this reflected energy is Doppler frequency shifted and is indicative of the patient's blood flow being sampled. Since the Q factor of the transducer 56 is increased, it has a narrow frequency band width, and hence, noise falling outside the band width is filtered out by the transducer.

With the present invention, the transducer 56 effectively serves three functions. First, it converts between mechanical acoustic energy and electrical energy; second, it internally accomplishes heterodyning of the transmitted ultrasonic frequency signal and the Doppler frequency shifted ultrasonic signal reflected back to the transducer from within the patient's body; and third, it filters out noise. This latter function is enhanced by increasing the Q factor of the transducer 56. As previously described, other aspects of the transducer assembly 16 also add to increasing the Q factor of the transducer. By using even number quarter-wave lengths for the thickness of the front wall 39, the reflection of ultrasonic energy in phase also effectively raises the impedance of the transducer 56, hence the return Doppler frequency shifted signal produced from reflections within the patient's body encounters the high impedance of the transducer and therefore produces a higher voltage output which is more easily measured by the detector 78. It is noted that with the blood flow detector 10 of the present invention running in a continuous wave mode using a single transducer 56, it is required to have not only good impedance matching to transmit energy from the transducer, but also to have a high impedance transducer so that the return reflected energy results in a measurable voltage signal across the transducer.

Another advantage of the present invention is that the detector 78 does not require any preamplification stage and detection of the un-amplified amplitude modulated signal on the transducer 56 is achieved using only the diode D1. Because of the high impedance, and hence the high voltage on the transducer 56, amplification is not necessary in the detector 78 and the signal on the transducer can be read directly, thus avoiding the need for an inherently noisy transistor amplifier in the detector.

With reference to FIG. 7, the detector includes the previously referred to diode D1 which has its cathode connected to a common terminal of a resistor R2 and a capacitor C4, which are connected in parallel and have their other terminal connected to ground. The diode D1, the resistor R2 and the capacitor C4 form the detector 78 which is a simple, half-way detector for the amplitude modulated signal produced by the transducer 56. The diode D1 passes one-half of the modulated envelope produced by the transducer 56, and the capacitor C4 bypasses the high frequency component to ground. The resistor R2 bleeds the voltage on the capacitor C4 to prevent the combination of the diode D1 and the capacitor C4 from acting as a peak detector. The time constant of the RC circuit comprising the resistor R2 and the capacitor C4 sets the first low pass pole frequency.

The output of the detector 78 is provided to an amplifier 80. The anode of the diode D1 is connected through a capacitor C5 to the base of a transistor Q2. The common terminal of the capacitor C5 and the base of the transistor Q2 is connected through a resistor R2 to ground. The RC circuit comprising the resistor R3 and the capacitor C5 form a high pass pole. The capacitor C5 also functions as a DC blocking capacitor. The resistor R3 also functions as a voltage divider in series with a pair of resistors R9 and R10 to set the DC bias presented to the output of the amplifier 80. The amplifier 80 further includes transistors Q3 and Q4, and resistors R4 and R5. The transistors Q2, Q3 and Q4, and the resistors R4 and R5 form, in combination, a conventional DC coupled cascaded amplifier.

Because of the relative frequencies and magnitudes of the signal and motion artifact voltages, in the past it has been very difficult to get good low frequency responses without being swamped by motion artifact. Standard high pass filtration techniques do not provide good separation unless several stages are cascaded. With the present invention, this problem is solved with a "Tee" RC filter circuit comprising the resistors R9 and R10, and a capacitor C9. When motion artifacts are present, the large voltages are passed back to the input 180° out of phase. This correction voltage drives the amplifier back into the linear range of operation. Equivalent separation of motion artifact using a standard filter would require a filter with a 68 dB per octive skirt.

The output of the amplifier 80 is provided to an audio output circuit 82. The audio output circuit 82 includes the previously referred to speaker 26 and variable resistance pot 36 for making volume adjustment settings necessary to provide a comfortable volume level for the user. The speaker 26 is driven by the final amplifier stage of the amplifier 80, comprising the transistor Q4. A resistor R7 and a capacitor C7 provide power supply decoupling. A resistor R6 and a capacitor C6 linearize the response of the speaker 26.

By use of a single transducer 56 operating in a continuous wave mode, both transmitting and receiving the return signal on the same transducer simultaneously, the transmit and receive energy beams of the blood flow detector 10 of the present invention are colinear. This eliminates the problems encountered in the past with two transducer continuous wave systems using parallel beam paths and with such systems using lensing to provide a beam cross-over point. Increased reflective energy from within the patient's body is realized, and focusing problems are eliminated. Moreover, the problems encountered with a single transducer operating in a pulsed mode are also eliminated, including the problem of the pulse rate limiting the reception window available and hence the depth range of optimum reception. Moreover, the blood flow detector 10 provides increased penetration and increased signal-to-noise ratio with more consistent performance over a range of penetration depths as compared with prior art blood flow detectors of generally equivalent size and cost.

The blood flow detector 10 of the present invention provides a sharp and small ultrasonic beam cross-section, and as a result spacial resolution and definition are improved. The combined characteristics of beam definition and sensitivity at a broad range of penetration depths makes the blood flow detector 10 extremely valuable when it is necessary to separate the flow patterns in adjacent vessels. This is important in a majority of vascular analysis and testing situations. The blood flow detector 10 also has the ability to detect far lower volumes and smaller vessels than with prior art blood flow detectors. The blood flow detector 10 has a relatively less complex design than prior art blood flow detectors, and hence can be manufactured at a lower cost. As a result, a relatively inexpensive, small and very responsive diagnostic aid is provided for evaluation of vascular dysfunctions.

In the presently preferred embodiment of the invention, the following values of resistance, capacitance, and inductance may be used, and where provided the following components identified by part number may be used. It will be understood by those of ordinary skill in the electronics art that the invention is not limited to circuitry using the specific values set forth herein or to the use of the specific components set forth herein:

| Resistor | 1K ⅛ watt | R1 |
|---|---|---|
| Resistor | 100K ⅛ watt | R2, R4, R5, R9, R10 |
| Resistor | 200K ⅛ watt | R3 |
| Resistor | 0.47K ⅛ watt | R6, R7 |
| Resistor | 10K ⅛ watt | resistor pot 36 |
| Capacitor | 7-30 picofarad | C1 |
| Capacitor | 66 picofarad | C2 |
| Capacitor | 22 picofarad | C3 |
| Capacitor | 0.01 microfarad | C4, C5 |
| Capacitor | 1.0 microfarad | C6 |
| Capacitor | 22 microfarad | C7 |
| Capacitor | 22 picofarad | C8 |
| Capacitor | 2.2 microfarad | C9 |
| Inductor | 33 microhenry | L1 |
| Inductor | 29 microhenry | L2 |
| Inductor | 8.2 microhenry | L3 |
| Diode 1n3004 | | D1 |
| Transistor Vn1304 | | Q1 |
| Transistor Vn0106 | | Q2, Q3 |
| Transistor Vn1306 | | Q4 |

It will be appreciated that, although specific embodiments of the invention have been described herein for purposes of illustration, various modifications may be made without departing from the spirit and scope of the invention. Accordingly, the invention is not limited except as by the appended claims.

I claim:

1. An ultrasonic, transcutaneous blood flow detector for detecting the blood flow in a patient's body, comprising:
   a transducer mounting member having an exterior face positionable against the skin of the patient for the transfer of ultrasonic energy into and out of the patient's body, and an opposite interior face;
   a single piezoelectric transducer having a first face in juxtaposition with said mounting member interior face, and an opposite second face, said transducer being movable laterally and axially relative to said mounting member within at least a range sufficient to permit substantially uninhibited deformation of said transducer in response to an electrical drive signal applied thereto and received ultrasonic acoustic energy reflected from within the patient's body;
   a film of viscous semifluid material positioned between said transducer first face and said mounting member interior face to couple ultrasonic energy between said transducer and said mounting member;
   a resilient member resiliently biasing said transducer first face into engagement with said mounting member interior face and said film of viscous semifluid material therebetween;
   transmitter means connected to said transducer for supplying said drive signal to said transducer, said drive signal being a continuous wave excitation signal causing said transducer to continuously transmit an acoustic output signal at a desired transmitted ultrasonic frequency;
   detector means connected to said transducer and operating concurrently with said transmitter means for detecting a Doppler frequency shifted electrical signal generated by said transducer as a result of Doppler frequency shifted acoustic energy reflected back to said transducer from within the patient's body indicative of blood flow, and for generating a detector signal in response thereto indicative of the velocity changes of the detected blood flow; and
   output means connected to said detector means for providing an output signal to the user responsive to said detector signal to indicate to the user the detected blood flow, whereby the blood flow detector operates with a single transducer continuously transmitting said acoustic output signal while concurrently detecting any Doppler frequency shifted acoustic energy reflected back to said transducer, with said transmitted acoustic output signal and said Doppler frequency shifted acoustic reflected energy traveling along the same path between said transducer and the area of reflection within the patient's body.

2. The blood flow detector of claim 1 wherein said mounting member includes an annular sidewall extending about the perimeter of said transducer and defining an interior chamber, and a pedestal positioned generally centrally within said chamber extending away from said exterior face and terminating in said interior face, said pedestal defining an inward annular wall extending between said pedestal and said sidewall, and spaced away from said interior face toward said exterior face, said sidewall being spaced away from a perimeter edge wall of said transducer to provide a free edge-space therebetween, said pedestal interior face being sized smaller than said transducer first face to provide said transducer first face with an annular edge surface portion extending laterally beyond said interior face, said annular edge surface portion of said transducer first face being held spaced away from said inward annular wall, whereby the Q factor of said transducer is increased.

3. The blood flow detector of claim 2 wherein said mounting member includes an end wall member attached to said sidewall and spaced away from said transducer to provide an air space therebetween, and wherein said resilient member is positioned between said end wall member and said transducer in yieldable engagement with both to resiliently bias said transducer first face into engagement with said mounting member interior face with said film of viscous semifluid material therebetween.

4. The blood flow detector of claim 3 wherein said resilient member is substantially inactive at said transmitted ultrasonic frequency of said acoustic output signal.

5. The blood flow detector of claim 1 wherein said interior and exterior faces of said mounting member are separated by an even number of quarter-wave lengths of said acoustic output signal, whereby ultrasonic energy of said acoustic output signal transmitted by said transducer which fails to cross the boundary between said exterior face and the patient's body against which said exterior face is positioned is reflected back to said transducer in phase thus increasing the impedance and Q factor of said transducer.

6. The blood flow detector of claim 1 wherein said resilient member is a resilient foam.

7. The blood flow detector of claim 1 wherein said resilient member is a spring.

8. The blood flow detector of claim 1 wherein said output signal is a variable pitch audible tone, and said output means includes means for converting said detector signal into said audible tone with variations in pitch being responsive to said detector signal indicating velocity changes of the detected blood flow.

9. The blood flow detector of claim 8 wherein said output means includes an earpiece positionable at the user's ear for transmitting said audible tone to the user's ear.

10. The blood flow detector of claim 9 wherein said output means includes an audio speaker and said earpiece is a hollow acoustic tube acoustically coupled at one end to said speaker.

11. The blood flow detector of claim 1 wherein said transmitter means is a substantially constant current generator having a high output impedance relative to said transducer, whereby said transducer is driven by a high impedance drive source.

12. The blood flow detector of claim 1 wherein said transmitter means includes:
an oscillator providing an output signal; and
an impedance transformer connected to said oscillator, said transformer transforming said oscillator output signal to a high voltage, low current signal comprising said transducer drive signal and having an output voltage variable in response to loading of said transducer.

13. The blood flow detector of claim 12 wherein said impedance transformer includes an inductor connected in series between said oscillator and said transducer, and a capacitor connected in parallel with said transducer and operating with said inductor to form a high impedance drive circuit to said transducer, whereby noise generated by said oscillator is supplied to said transducer at high impedance, and if outside the resonant frequency domain of said transducer are effectively filtered out by said transducer's mechanical nonresponsiveness thereto.

14. The blood flow detector of claim 12 wherein said oscillator output signal is at a substantially constant current.

15. The blood flow detector of claim 1 wherein said transmitter means includes means for providing said drive signal to said transducer having an output voltage variable in response to loading of said transducer with reflective energy, with the frequency of said drive signal being automatically variable in response to variations in the loading of said transducer to achieve optimum operational frequency of said transducer within a range of optimum operational frequencies.

16. An ultransonic, transcutaneous blood flow detector for detecting the blood flow in a patient's body, comprising:

a protective transducer mounting cup having an exterior face positionable against the skin of the patient for the transfer of ultrasonic energy into and out of the patient's body, and an opposite interior face substantially parallel with said exterior face, said mounting cup further having an annular sidewall defining an interior chamber, and a pedestal positioned generally centrally within said chamber extending away from said exterior face and terminating in said interior face;

a single piezoelectric transducer positioned within said mounting cup interior chamber, and having a first face mounted in juxtaposition with said mounting cup interior face, and an opposite second face, said transducer being movable laterally and axially relative to said mounting cup within at least a range sufficient to permit substantially uninhibited deformation of said transducer in response to an electrical drive signal applied thereto and received ultrasonic acoustic energy reflected from within the patient's body;

a film of viscous semifluid material positioned between said transducer first face and said mounting cup interior face to couple ultrasonic energy between said transducer and said mounting cup;

a resilient member resiliently biasing said transducer first face into engagement with said mounting cup interior face with said film of viscous semifluid material therebetween;

transmitter means connected to said transducer for supplying said drive signal to said transducer, said drive signal being a continuous wave excitation signal causing said transducer to continuously transmit an acoustic output signal at a desired transmitted ultrasonic frequency, said transmitter means including drive means for providing said drive signal to said transducer having an output voltage variable in response to loading of said transducer with reflective energy, with the frequency of said drive signal being automatically variable in response to variations in the loading of said transducer to achieve optimum operational frequency of said transducer within a range of optimum operational frequencies;

detector means connected to said transducer and operating concurrently with said transmitter means for detecting a Doppler frequency shifted electrical signal generated by said transducer as a result of Doppler frequency shifted acoustic energy reflected back to said transducer from within the patient's body indicative of blood flow, and for generating a detector signal in response thereto indicative of the velocity changes of the detected blood flow; and output means connected to said detector means for providing an output signal to the user responsive to said detector signal to indicate to the user the detected blood flow, whereby the blood flow detector operates with a single transducer continuously transmitting said acoustic output signal while concurrently detecting any Doppler frequency shifted acoustic energy reflected back to said transducer, with said transmitted acoustic output signal and said Doppler frequency shifted acoustic reflected energy traveling along the same straight-line path between said transducer and the area of reflection within the patient's body.

17. The blood flow detector of claim 16 wherein said mounting cup pedestal and sidewall define an inward annular wall extending between said pedestal and said sidewall, spaced away from said interior face toward said exterior face, said sidewall being laterally spaced away from a perimeter edge wall of said transducer to provide a free edge-space therebetween.

18. The blood flow detector of claim 17 wherein said pedestal interior face is sized smaller than said transducer first face to provide said transducer first face with an annular edge portion extending laterally beyond said interior face, said annular edge portion of said transducer first face being held spaced away from said inward annular wall.

19. The blood flow detector of claim 16 wherein said mounting cup includes an end wall closing said interior chamber and attached to said sidewall, said end wall being spaced away from said transducer to provide an air space therebetween, and wherein said resilient member is positioned in said interior chamber between said end wall and said transducer in yieldable engagement with both to resiliently bias said transducer first face into engagement with said mounting cup interior face with said film of viscous semifluid material therebetween.

20. The blood flow detector of claim 19 wherein said resilient member is substantially inactive at said transmitted ultrasonic frequency of said acoustic output signal.

21. The blood flow detector of claim 16 wherein said interior and exterior faces of said mounting cup are separated by an even number of quarter-wave lengths of said acoustic output signal, whereby ultrasonic energy of said acoustic output signal transmitted by said transducer which fails to cross the boundary between said exterior face and the patient's body against which said exterior face is positioned is reflected back to said transducer in phase thus increasing the impedance and Q factor of said transducer.

22. The blood flow detector of claim 16 wherein said output signal is a variable pitch audible tone, and said output means includes means for converting said detector signal into said audible tone with variations in pitch being responsive to said detector signal indicating velocity changes of the detected blood flow, and an earpiece positionable at the user's ear for transmitting said audible tone to the user's ear.

23. The blood flow detector of claim 16 wherein said drive means includes:
an oscillator providing an output signal; and
an impedance transformer connected to said oscillator, said transformer transforming said oscillator output signal to a high voltage, low current signal comprising said transducer drive signal and having an output voltage variable in response to loading of said transducer.

24. The blood flow detector of claim 23 wherein said impedance transformer includes an inductor connected in series between said oscillator and said transducer, and a capacitor connected in parallel with said transducer and operating with said inductor to form a high impedance drive circuit to said transducer, whereby noise generated by said oscillator is supplied to said transducer at high impedance, and if outside the resonant frequency domain of said transducer are effectively filtered out by said transducer's mechanical nonresponsiveness thereto.

25. The blood flow detector of claim 24 wherein said oscillator output signal is at a substantially constant current.

26. An ultransonic, flow detector for detecting the flow of fluid in a body, comprising:
a single piezoelectric transducer for the transfer of ultrasonic energy into and out of the body, said transducer being deformable in response to an electrical drive signal applied thereto and received ultrasonic acoustic energy reflected from within the body;
transmitter means connected to said transducer for supplying said drive signal to said transducer, said drive signal being a continuous wave excitation signal causing said transducer to continuously transmit an acoustic output signal at a desired transmitted ultrasonic frequency;
detector means connected to said transducer and operating concurrently with said transmitter means for detecting a Doppler frequency shifted electrical signal generated by said transducer as a result of Doppler frequency shifted acoustic energy reflected back to said transducer from within the body indicative of fluid flow, and for generating a detector signal in response thereto indicative of the velocity changes of the detected fluid flow; and
output means connected to said detector means for providing an output signal to the user responsive to said detector signal to indicate to the user the detected fluid flow, whereby the flow detector operates with a single transducer continuously transmitting said acoustic output signal while concurrently detecting any Doppler frequency shifted acoustic energy reflected back to said transducer, with said transmitted acoustic output signal and said Doppler frequency shifted acoustic reflected energy traveling along the same path between said transducer and the area of reflection within the body.

27. The flow detector of claim 26 further including a transducer mounting member having an exterior face positionable against the body for the transfer of ultrasonic energy into and out of the body, and an opposite interior face, and wherein said transducer has a first face in juxtaposition with said mounting member interior face, and an opposite second face, said interior and exterior faces of said mounting member being separated by an even number of quarter-wave lengths of said acoustic output signal, whereby ultrasonic energy of said acoustic output signal transmitted by said transducer which fails to cross the boundary between said exterior face and the body against which said exterior face is positioned is reflected back to said transducer in phase thus increasing the impedance and Q factor of said transducer.

28. The flow detector of claim 26 wherein said transmitter means is a substantially constant current generator having a high output impedance relative to said transducer, whereby said transducer is driven by a high impedance drive source.

29. The flow detector of claim 26 wherein said transmitter means includes:
an oscillator providing an output signal; and
an impedance transformer connected to said oscillator, said transformer transforming said oscillator output signal to a high voltage, low current signal comprising said transducer drive signal and having an output voltage variable in response to loading of said transducer.

30. The flow detector of claim 29 wherein said impedance transformer includes an inductor connected in series between said oscillator and said transducer, and a capacitor connected in parallel with said transducer and operating with said inductor to form a high impedance drive circuit to said transducer, whereby noise generated by said oscillator is supplied to said transducer at high impedance, and if outside the resonant frequency domain of said transducer are effectively filtered out by said transducer's mechanical nonresponsiveness thereto.

31. The flow detector of claim 29 wherein said oscillator output signal is at a substantially constant current.

32. The flow detector of claim 26 wherein said transmitter means includes means for providing said drive signal to said transducer having an output voltage variable in response to loading of said transducer with reflective energy, with the frequency of said drive signal being automatically variable in response to variations in the loading of said transducer to achieve optimum operational frequency of said transducer within a range of optimum operational frequencies.

33. An ultrasonic, flow detector for detecting the flow of fluid in a body, comprising:
   a single piezoelectric transducer for the transfer of ultrasonic energy into and out of the body, said transducer being deformable in response to an electrical drive signal applied thereto and received ultrasonic acoustic energy reflected from within the body;
   transmitter means connected to said transducer for supplying said drive signal to said transducer, said drive signal being a continuous wave excitation signal causing said transducer to continuously transmit an acoustic output signal at a desired transmitted ultrasonic frequency;
   detector means connected to said transducer and operating concurrently with said transmitter means for detecting a Doppler frequency shifted electrical signal generated by said transducer as a result of Doppler frequency shifted acoustic energy reflected back to sand transducer from within the body indicative of fluid flow, and for generating a detector signal in response thereto indicative of the velocity changes of the detected fluid flow;
   output means connected to said detector means for providing an output signal to the user responsive to said detector signal to indicate to the user the detected fluid flow, whereby the flow detector operates with a single while continuously transmitting said acoustic output signal while concurrently detecting any Doppler frequency shifted acoustic energy reflected back to said transducer, with said transmitted acoustic output signal and said Doppler frequency shifted acoustic reflected energy traveling along the same path between said transducer and the area of reflection within the body;
   said transducer having a first face and an opposite second face, and
   a transducer mounting member having an exterior face positionable against the body for the transfer of ultrasonic energy into and out of the body, and an opposite interior face, said mounting member interior face and said transducer first face being positioned in juxtaposition with said transducer being movable laterally and axially relative to said mounting member within at least a range sufficient to permit substantially uninhibited deformation of said transducer in response to said drive signal applied thereto and received ultrasonic acoustic energy reflected from within the body;
   a film of viscous semifluid material positioned between said transducer first face and said mounting member interior face to couple ultrasonic energy between said transducer and said mounting member; and
   a resilient member resiliently biasing said transducer first face into engagement with said mounting member interior face with said film of viscous semifluid material therebetween.

34. The flow detector of claim 33 wherein said mounting member includes an annular sidewall extending about the perimeter of said transducer and defining an interior chamber, and a pedestal positioned generally centrally within said chamber extending away from said exterior face and terminating in said interior face, said pedestal defining an inward annular wall extending between said pedestal and said sidewall, and spaced away from said interior face toward said exterior face, said sidewall being spaced away from a perimeter edge wall of said transducer to provide a free edge-space therebetween, said pedestal interior face being sized smaller than said transducer first face to provide said transducer first face with an annular edge surface portion extending laterally beyond said interior face, said annular edge surface portion of said transducer first face being held spaced away from said inward annular wall, whereby the Q factor of said transducer is increased.

35. The flow detector of claim 34 wherein said mounting member includes an end wall member attached to said sidewall and spaced away from said transducer to provide an air space therebetween, and wherein said resilient member is positioned between said end wall member and said transducer in yieldable engagement with both to resiliently bias said transducer first face into engagement with said mounting member interior face with said film of viscous semifluid material therebetween.

36. The flow detector of claim 35 wherein said resilient member is substantially inactive at said transmitted ultrasonic frequency of said acoustic output signal.

* * * * *